(12) United States Patent
Karst et al.

(10) Patent No.: US 8,728,059 B2
(45) Date of Patent: May 20, 2014

(54) SYSTEM AND METHOD FOR ASSURING VALIDITY OF MONITORING PARAMETER IN COMBINATION WITH A THERAPEUTIC DEVICE

(75) Inventors: Edward Karst, South Pasadena, CA (US); Clark R. Baker, Jr., Newman, CA (US)

(73) Assignee: Covidien LP, Mansfield, MA (US)

(*) Notice: Subject to any disclaimer, the term of this patent is extended or adjusted under 35 U.S.C. 154(b) by 792 days.

(21) Appl. No.: 11/541,302

(22) Filed: Sep. 29, 2006

(65) Prior Publication Data
US 2008/0114211 A1 May 15, 2008

(51) Int. Cl.
*A61K 9/22* (2006.01)

(52) U.S. Cl.
USPC ........ 604/890.1; 604/65; 604/67; 128/204.18; 600/306; 600/309; 600/340; 600/365; 600/449; 600/453; 600/454; 600/455; 600/456; 600/468; 600/465; 600/481; 600/482; 600/485; 600/504; 600/533; 600/538; 600/547; 600/561; 600/202; 600/363; 600/364

(58) Field of Classification Search
USPC ................... 604/65, 67, 890.1; 128/204.18; 600/306, 309, 340, 365, 449, 453–456, 600/468, 465, 481–482, 485, 504, 533, 538, 600/547, 561, 202, 363, 364
See application file for complete search history.

(56) References Cited

U.S. PATENT DOCUMENTS

| | | | | |
|---|---|---|---|---|
| 2,888,922 | A * | 6/1959 | Bellville | 128/204.23 |
| 3,638,640 | A | 2/1972 | Shaw | |
| 3,923,060 | A * | 12/1975 | Ellinwood, Jr. | 604/891.1 |
| 4,116,238 | A * | 9/1978 | Pettijohn | 604/21 |
| RE30,317 | E * | 7/1980 | Lubbers et al. | 600/363 |
| 4,445,514 | A * | 5/1984 | Osterholm | 600/363 |
| 4,714,341 | A | 12/1987 | Hamaguri et al. | |
| 4,805,623 | A | 2/1989 | Jöbsis | |
| 4,807,631 | A | 2/1989 | Hersh et al. | |
| 4,889,116 | A | 12/1989 | Taube | |
| 4,911,167 | A | 3/1990 | Corenman et al. | |

(Continued)

FOREIGN PATENT DOCUMENTS

| | | |
|---|---|---|
| DE | 19647877 | 5/1998 |
| EP | 0549685 | 9/1991 |

(Continued)

OTHER PUBLICATIONS

Azhar, N., et al.; "Automatic Feedback Control of Oxygen Therapy Using Pulse Oximetry," Annual International Conference of the IEEE Engineering in Medicine and Biology Society, vol. 13, No. 4, pp. 1614-1615 (1991).

(Continued)

*Primary Examiner* — Nicholas Lucchesi
*Assistant Examiner* — Scott Medway
(74) *Attorney, Agent, or Firm* — Fletcher Yoder PC

(57) ABSTRACT

The disclosed embodiments relate to a system and method for assuring validity of monitoring parameters in combination with a therapeutic device. An exemplary embodiment of the present technique comprises perturbing a treatment administered to a patient, measuring at least one parameter of the patient reflecting the underlying physiological state and associated with the treatment, and comparing the perturbations of the treatment to measurements of the at least one parameter to determine if the perturbations to the treatment are reflected by the parameter.

13 Claims, 3 Drawing Sheets

(56) References Cited

U.S. PATENT DOCUMENTS

| | | | |
|---|---|---|---|
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,005,571 A * | 4/1991 | Dietz | 128/205.25 |
| 5,028,787 A | 7/1991 | Rosenthal et al. | |
| 5,065,749 A | 11/1991 | Hasebe et al. | |
| 5,084,327 A | 1/1992 | Stengel | |
| 5,119,815 A | 6/1992 | Chance | |
| 5,122,974 A | 6/1992 | Chance | |
| 5,167,230 A | 12/1992 | Chance | |
| 5,190,038 A | 3/1993 | Polson et al. | |
| 5,207,752 A * | 5/1993 | Sorenson et al. | 604/20 |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,355,880 A | 10/1994 | Thomas et al. | |
| 5,365,922 A | 11/1994 | Raemer | |
| 5,372,136 A | 12/1994 | Steuer et al. | |
| 5,380,272 A * | 1/1995 | Gross | 604/20 |
| 5,385,143 A | 1/1995 | Aoyagi | |
| 5,390,670 A | 2/1995 | Centa et al. | |
| 5,413,099 A | 5/1995 | Schmidt et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,553,614 A | 9/1996 | Chance | |
| 5,564,417 A | 10/1996 | Chance | |
| 5,575,285 A | 11/1996 | Takanashi et al. | |
| 5,609,576 A * | 3/1997 | Voss et al. | 604/67 |
| 5,611,337 A | 3/1997 | Bukta | |
| 5,630,413 A | 5/1997 | Thomas et al. | |
| 5,645,059 A | 7/1997 | Fein et al. | |
| 5,645,060 A | 7/1997 | Yorkey | |
| 5,680,857 A | 10/1997 | Pelikan et al. | |
| 5,682,877 A | 11/1997 | Mondry | |
| 5,692,503 A | 12/1997 | Keunstner | |
| 5,730,124 A | 3/1998 | Yamauchi | |
| 5,758,644 A | 6/1998 | Diab et al. | |
| 5,779,631 A | 7/1998 | Chance | |
| 5,782,757 A | 7/1998 | Diab et al. | |
| 5,786,592 A | 7/1998 | Hök | |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 5,997,501 A * | 12/1999 | Gross et al. | 604/65 |
| 6,011,986 A | 1/2000 | Diab et al. | |
| 6,064,898 A | 5/2000 | Aldrich | |
| 6,081,742 A | 6/2000 | Amano et al. | |
| 6,088,607 A | 7/2000 | Diab et al. | |
| 6,120,460 A | 9/2000 | Abreu | |
| 6,131,571 A * | 10/2000 | Lampotang et al. | 128/204.21 |
| 6,134,460 A | 10/2000 | Chance | |
| 6,150,951 A | 11/2000 | Olejniczak | |
| 6,154,667 A | 11/2000 | Miura et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,183,418 B1 * | 2/2001 | Kuennecke | 600/363 |
| 6,230,035 B1 | 5/2001 | Aoyagi et al. | |
| 6,247,470 B1 * | 6/2001 | Ketchedjian | 128/200.28 |
| 6,258,032 B1 * | 7/2001 | Hammesfahr | 600/454 |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,353,750 B1 | 3/2002 | Kimura et al. | |
| 6,390,091 B1 | 5/2002 | Banner et al. | |
| 6,391,015 B1 * | 5/2002 | Millot | 604/503 |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,431,171 B1 | 8/2002 | Burton | |
| 6,438,399 B1 | 8/2002 | Kurth | |
| 6,461,305 B1 | 10/2002 | Schnall | |
| 6,466,809 B1 | 10/2002 | Riley | |
| 6,475,180 B2 * | 11/2002 | Peterson et al. | 604/65 |
| 6,487,439 B1 | 11/2002 | Skladnev et al. | |
| 6,488,623 B1 * | 12/2002 | Ozarowski et al. | 600/363 |
| 6,501,974 B2 | 12/2002 | Huiku | |
| 6,501,975 B2 | 12/2002 | Diab et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,561,187 B2 | 5/2003 | Schmidt et al. | |
| 6,580,086 B1 | 6/2003 | Schulz et al. | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,631,716 B1 | 10/2003 | Robinson et al. | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,671,529 B2 | 12/2003 | Claure et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,709,402 B2 | 3/2004 | Dekker | |
| 6,711,424 B1 | 3/2004 | Fine et al. | |
| 6,711,425 B1 | 3/2004 | Reuss | |
| 6,714,245 B1 | 3/2004 | Ono | |
| 6,723,086 B2 * | 4/2004 | Bassuk et al. | 604/890.1 |
| 6,731,274 B2 | 5/2004 | Powell | |
| 6,773,397 B2 | 8/2004 | Kelly | |
| 6,785,568 B2 | 8/2004 | Chance | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,807,965 B1 * | 10/2004 | Hickle | 128/204.23 |
| 6,829,496 B2 | 12/2004 | Nagai et al. | |
| 6,832,200 B2 * | 12/2004 | Greeven et al. | 705/3 |
| 6,850,053 B2 | 2/2005 | Daalmans et al. | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,993,371 B2 | 1/2006 | Kiani et al. | |
| 6,996,427 B2 | 2/2006 | Ali et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,047,056 B2 | 5/2006 | Hannula et al. | |
| 7,066,173 B2 | 6/2006 | Banner et al. | |
| 7,127,278 B2 | 10/2006 | Melker et al. | |

(56) References Cited

U.S. PATENT DOCUMENTS

| | | | |
|---|---|---|---|
| 7,137,975 B2 * | 11/2006 | Miller et al. | 604/501 |
| 7,162,306 B2 | 1/2007 | Caby et al. | |
| 7,209,775 B2 | 4/2007 | Bae et al. | |
| 7,210,478 B2 | 5/2007 | Banner et al. | |
| 7,236,811 B2 | 6/2007 | Schmitt | |
| 7,246,618 B2 | 7/2007 | Habashi | |
| 7,263,395 B2 | 8/2007 | Chan et al. | |
| 7,272,426 B2 | 9/2007 | Schmid | |
| 7,373,193 B2 | 5/2008 | Al-Ali et al. | |
| 7,398,115 B2 | 7/2008 | Lynn | |
| 7,490,608 B2 * | 2/2009 | Brown et al. | 128/207.11 |
| 7,708,731 B2 * | 5/2010 | Riddle et al. | 604/501 |
| 7,885,709 B2 * | 2/2011 | Ben-David | 607/2 |
| 7,937,143 B2 * | 5/2011 | Demarais et al. | 604/21 |
| 7,938,797 B2 * | 5/2011 | Estes | 604/66 |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |
| 2001/0044700 A1 | 11/2001 | Kobayashi et al. | |
| 2002/0017299 A1 * | 2/2002 | Hickle | 128/204.21 |
| 2002/0026106 A1 | 2/2002 | Khalil et al. | |
| 2002/0035318 A1 | 3/2002 | Mannheimer et al. | |
| 2002/0038079 A1 | 3/2002 | Steuer et al. | |
| 2002/0042558 A1 | 4/2002 | Mendelson | |
| 2002/0049389 A1 | 4/2002 | Abreu | |
| 2002/0062071 A1 | 5/2002 | Diab et al. | |
| 2002/0111748 A1 | 8/2002 | Kobayashi et al. | |
| 2002/0133068 A1 | 9/2002 | Huiku | |
| 2002/0156354 A1 | 10/2002 | Larson | |
| 2002/0161287 A1 | 10/2002 | Schmitt | |
| 2002/0161290 A1 | 10/2002 | Chance | |
| 2002/0165439 A1 | 11/2002 | Schmitt | |
| 2002/0183682 A1 * | 12/2002 | Darvish et al. | 604/20 |
| 2002/0198443 A1 | 12/2002 | Ting | |
| 2003/0023140 A1 | 1/2003 | Chance | |
| 2003/0055324 A1 | 3/2003 | Wasserman | |
| 2003/0060693 A1 | 3/2003 | Monfre et al. | |
| 2003/0106553 A1 * | 6/2003 | Vanderveen | 128/204.18 |
| 2003/0139687 A1 | 7/2003 | Abreu | |
| 2003/0144584 A1 | 7/2003 | Mendelson | |
| 2003/0220548 A1 | 11/2003 | Schmitt | |
| 2003/0220576 A1 | 11/2003 | Diab | |
| 2004/0010188 A1 | 1/2004 | Wasserman | |
| 2004/0054270 A1 | 3/2004 | Pewzner et al. | |
| 2004/0059212 A1 * | 3/2004 | Abreu | 600/373 |
| 2004/0087846 A1 | 5/2004 | Wasserman | |
| 2004/0107065 A1 | 6/2004 | Al-Ali | |
| 2004/0127779 A1 | 7/2004 | Steuer et al. | |
| 2004/0171920 A1 | 9/2004 | Mannheimer et al. | |
| 2004/0176670 A1 | 9/2004 | Takamura et al. | |
| 2004/0176671 A1 | 9/2004 | Fine et al. | |
| 2004/0230106 A1 | 11/2004 | Schmitt et al. | |
| 2004/0242976 A1 * | 12/2004 | Abreu | 600/315 |
| 2005/0043675 A1 * | 2/2005 | Pastore et al. | 604/67 |
| 2005/0066969 A1 | 3/2005 | Rick et al. | |
| 2005/0080323 A1 | 4/2005 | Kato | |
| 2005/0101850 A1 | 5/2005 | Parker | |
| 2005/0109340 A1 | 5/2005 | Tehrani | |
| 2005/0113651 A1 | 5/2005 | Wood et al. | |
| 2005/0113656 A1 | 5/2005 | Chance | |
| 2005/0168722 A1 | 8/2005 | Forstner et al. | |
| 2005/0177034 A1 | 8/2005 | Beaumont | |
| 2005/0192488 A1 | 9/2005 | Bryenton et al. | |
| 2005/0203357 A1 | 9/2005 | Debreczeny et al. | |
| 2005/0228248 A1 | 10/2005 | Dietiker | |
| 2005/0247311 A1 | 11/2005 | Vacchiano | |
| 2005/0267346 A1 | 12/2005 | Faber et al. | |
| 2005/0277912 A1 * | 12/2005 | John | 604/890.1 |
| 2005/0283059 A1 | 12/2005 | Iyer et al. | |
| 2006/0009688 A1 | 1/2006 | Lamego et al. | |
| 2006/0015021 A1 | 1/2006 | Cheng | |
| 2006/0020181 A1 | 1/2006 | Schmitt | |
| 2006/0030763 A1 | 2/2006 | Mannheimer et al. | |
| 2006/0052680 A1 | 3/2006 | Diab | |
| 2006/0058683 A1 | 3/2006 | Chance | |
| 2006/0064024 A1 | 3/2006 | Schnall | |
| 2006/0155206 A1 | 7/2006 | Lynn | |
| 2006/0195028 A1 | 8/2006 | Hannula et al. | |
| 2006/0224058 A1 | 10/2006 | Mannheimer | |
| 2006/0247501 A1 | 11/2006 | Ali | |
| 2006/0258921 A1 | 11/2006 | Addison et al. | |
| 2006/0282001 A1 | 12/2006 | Noel et al. | |
| 2007/0000494 A1 | 1/2007 | Banner et al. | |
| 2007/0062531 A1 | 3/2007 | Fisher et al. | |
| 2007/0129647 A1 | 6/2007 | Lynn | |
| 2008/0076992 A1 | 3/2008 | Hete et al. | |
| 2008/0125700 A1 * | 5/2008 | Moberg et al. | 604/67 |
| 2009/0105605 A1 * | 4/2009 | Abreu | 600/549 |

FOREIGN PATENT DOCUMENTS

| | | |
|---|---|---|
| EP | 0548624 | 6/1993 |
| EP | 0615764 | 9/1994 |
| EP | 0702931 | 3/1996 |
| EP | 0996358 | 1/2002 |
| JP | 3115374 | 12/2000 |
| WO | WO8600234 | 1/1986 |
| WO | WO9404865 | 8/1993 |
| WO | WO9953834 | 10/1999 |
| WO | WO0021438 | 4/2000 |
| WO | WO0100264 | 7/2002 |
| WO | WO0100265 | 7/2002 |
| WO | WO2005065540 | 7/2005 |
| WO | WO2007015833 | 2/2007 |

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).

\* cited by examiner

SYSTEM AND METHOD FOR ASSURING VALIDITY OF MONITORING PARAMETER IN COMBINATION WITH A THERAPEUTIC DEVICE

BACKGROUND OF THE INVENTION

1. Field of the Invention

The present invention relates generally to monitoring parameters associated with a therapy, and more particularly, to systems and methods for assuring that a therapy is applied correctly and that a monitor accurately reflects an underlying physiological parameter.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics of a patient. Such devices provide doctors and other healthcare personnel with the information they need to provide the best possible healthcare for their patients. As a result, such monitoring devices have become an indispensable part of modern medicine.

There are many instances where patients are monitored for physiological parameters derived from measurements obtainable by various physiological sensors and monitors. Similarly, during a course of a treatment, a patient may further be coupled to therapeutic devices used to treat certain medical conditions, as prescribed by a health care provider. In fact, medical devices, such as a physiological monitoring system, may be coupled to a patient so as to monitor the efficacy of an administered therapy by a therapeutic device. Accordingly, it is expected that a certain therapy administered over time to a patient would have a direct effect on certain corresponding physiological parameters measurable by a monitoring system coupled to the patient.

Monitoring physiological signs of a patient, as well as properly administering therapies or treatments to a patient, may depend on the manner in which medical devices comprising monitoring systems and therapeutic devices are coupled to the patient. However, situations may arise where medical devices may be inappropriately coupled the patient, resulting in an improper administration of the treatment to the patient or incorrect monitoring of the patient's condition. For example, a therapeutic device may become detached from the patient while treatment may be ongoing, resulting in the termination of the therapy administered to the patient. Further, crowded hospital wards and emergency rooms where many patients may be in close proximity with one another may lead to occurrences of inadvertent swapping of sensors and/or therapeutic devices among the patients. Again, such occurrences are undesirable as improper monitoring and treatment of patients may result. In other instances, the therapeutic device or monitoring system may cease to function properly and some indication of this is desired.

SUMMARY

Certain aspects commensurate in scope with the claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a method including the acts of: perturbing a treatment administered to a patient; measuring at least one parameter indicative of the underlying physiological state of the patient associated with the treatment; and comparing the perturbations of the treatment to measurements of the at least one parameter to determine if the perturbations to the treatment are reflected by the parameter.

There is also provided a system including: a device adapted to administer a treatment, wherein the treatment is varied over time; and a monitoring system adapted to measure a parameter affected by the treatment such that the variations in the treatment are reflected in the measured parameter.

There is also provided a tangible machine readable medium including: code for perturbing a treatment administered to a patient; code for measuring at least one parameter indicative of the underlying physiological state of the patient associated with the treatment; and code for comparing the perturbations of the treatment to measurements of the at least one physiological parameter to determine if the perturbations to the treatment are reflected by the physiological parameter.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In one example of an implementation of the present technique, a therapeutic device, such as a ventilator or respirator, is used to treat a patient. In such an implementation, it would be desirable to have a control mechanism and method that would verify receipt of the specified treatment by the patient, such as by perturbing the therapy provided to the patient such that modulations in a monitored physiological parameter associated with the treatment given to the patient may be detected. Such a perturbation may be small enough so that the quality of the clinical treatment is not affected, yet substantial enough to be noticed by correlated modulations in the monitored physiological parameters. Hence, such a method would provide confirmation that the therapy is delivered properly, as well as assure that the sensor is making sensitive measurements.

Figure 1:
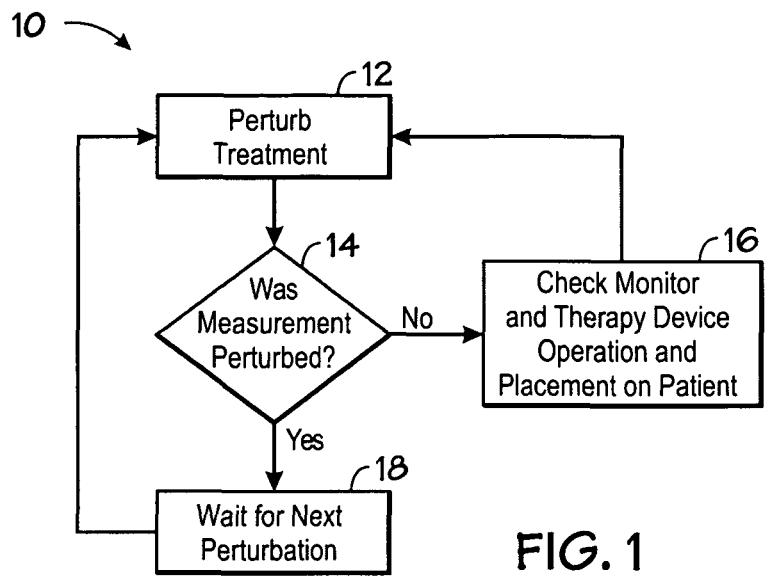
FIG. 1 is a block diagram of a method in accordance with an exemplary embodiment of the present technique.

Turning now to FIG. 1, a block diagram 10 in accordance with exemplary embodiments of the present technique is illustrated. The block diagram 10 describes a method of perturbing a therapy applied to a patient and subsequently monitoring a correlated modulation in a parameter associated with the applied therapy. The method described by the block diagram 10 may apply to perturbing therapies, such as respirator-delivered oxygen, airway pressure delivered by a respirator, delivery of insulin via an insulin pump, application of heat by a heating pad or warming blanket, delivery of cardiovascular drugs (such as cardioactive and/or vasoactive drugs) via infusion, delivery of anesthetic drugs via an anesthetic machine, delivery of antipyretic drugs, and so forth. Respective monitored physiological parameters associated with the above exemplary therapies include oxygen saturation, blood sugar levels, heart rate, etc.

The method begins at block 12 where a treatment given to a patient is perturbed. Thereafter, the method proceeds to decision block 14 where it is determined whether a corresponding measurement of a parameter associated with the treatment was perturbed. The determination may be made by a clinician who monitors the measurement of the parameter for an observable perturbation or by one or more devices, such as the monitoring device, that analyze the measurements for indications of the perturbation. As will be appreciated by those of ordinary skill in the art, such a device may be configured to observe or recognize perturbations that might be too small to be observed by a human. Absent any such observed perturbations in the monitored physiological parameter, a clinician or device may determine that the patient is not receiving the appropriate treatment due to problems associated with the therapy device, the manner in which it is applied to the patient, or the certainty that the monitored parameter reflects the patient's underlying physiological state. Accordingly, the method proceeds to block 16 where, in one implementation, the clinician may verify whether the therapeutic device is working properly and/or is appropriately attached to the patient. Further, at block 16 the clinician may check the placement and function of the monitoring device responsible for monitoring the respective physical parameters. Alternatively, in an implementation where a device makes the determination that the perturbation was not detected in the corresponding measured parameters, the device may be configured to provide a notification (such as by displaying a message or sounding an audible alarm) to a clinician. In such an implementation, the device, such as a monitoring device, may be configured to increase its measurement sensitivity and/or to automatically adjust the treatment in addition to or instead of providing a notification. For example, in one embodiment, the device, such as the monitoring device or therapeutic device, may adjust the treatment level by returning to the level of therapy delivered when a clinician was last present or to a predetermined level of treatment in the event that the perturbation is not detected. As one of ordinary skill in the art will appreciate, the decision to adjust the treatment level, such as by reverting to a prior treatment level, might be made after a predetermined period of time has elapsed during which the perturbation has not been detected. After doing so, the method returns to block 12 where a subsequent perturbation is again applied to the therapy.

Returning to decision block 14, if a perturbation in the measured parameter associated with the therapy is observed, it is an indication that the therapy is applied appropriately to the patient and is being properly monitored. Thus, the method proceeds to block 18, where the clinician or the monitor waits for a subsequent perturbation to appear in the monitored physiological parameter. In so doing, the method ensures repeated observation of the perturbations in the monitored parameter. Thus, the clinician or device may rely on the repeatable correlations existing between therapy and monitored perturbation. Thereafter, the method returns back to block 12 where a subsequent perturbation is applied to the therapy and the method commences again. In an exemplary implementation where the therapeutic and/or monitoring devices form a closed-loop physiological control system, the repeated detection of correlations between therapy and monitored perturbation provides an assurance of appropriate device interaction in the titration of therapy. Conversely, any cessation in correlation between therapy and monitor may indicate that closed-loop control of the therapy is not appropriate without attention by a clinician.

Figure 2A:
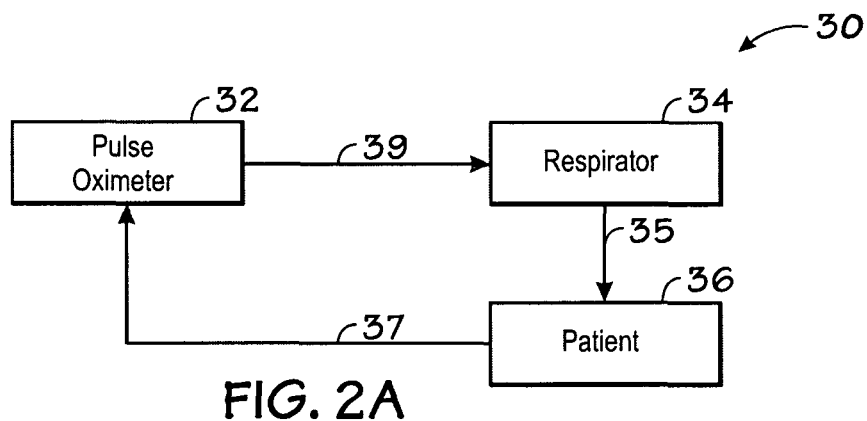
FIG. 2A is a block diagram of a system in accordance with an exemplary embodiment of the present technique.
Figure 2B:
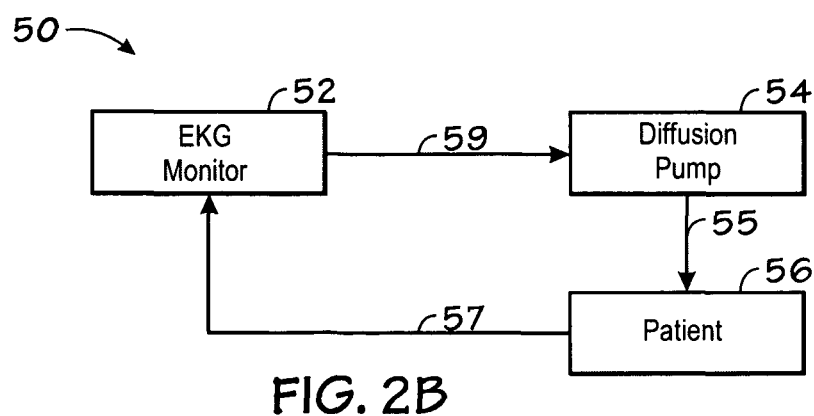
FIG. 2B is a block diagram of a system in accordance with an exemplary embodiment of the present technique.
Figure 2C:
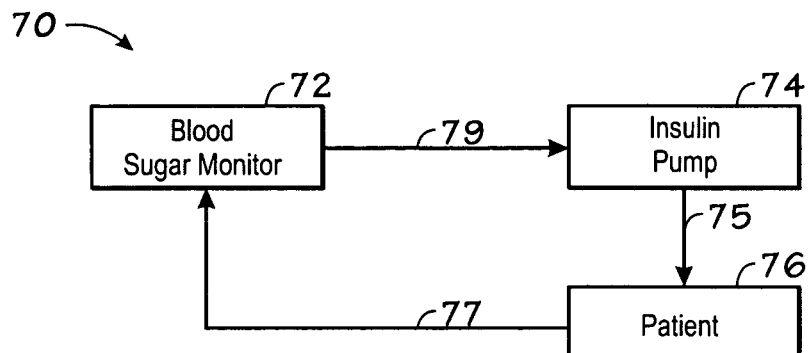
FIG. 2C is a block diagram of a system in accordance with an exemplary embodiment of the present technique.

FIGS. 2A-2C depict exemplary implementations in accordance with embodiments of the present technique. These figures illustrate exemplary system components for applying the above method 10. In particular, FIG. 2A illustrates a system 30 comprising a pulse oximeter 32 and a respirator 34 connected to a patient 36. The respirator 34 may apply a treatment by delivering a prescribed dose of oxygen directly to the airways of patient 36. The pulse oximeter 32 may be configured to acquire measurements of oxygen saturation ($SpO_2$) 37 levels, indicating the level of oxygen present in the blood stream and tissue of the patient 36. Thus, $SpO_2$ 37 would be considered in this case a parameter associated with and well correlated to the oxygen 35 delivered by the respirator 34. In an exemplary embodiment, a physician or a health care provider may want to apply a treatment to the patient 36 such that the respirator 34 may deliver a specific amount of oxygen 35 to the patient 36. Correspondingly, oxygen saturation levels measured by the pulse oximeter 32 should correlate with the specific levels of oxygen 35 delivered to the patient by the respirator 34, as prescribed by the clinician. Adjustment 39 of the operation of the respirator 34 based on the $SpO_2$ 37 measured by the pulse oximeter 32 provides a closed loop method of operation.

Such a feedback mechanism may be advantageously employed to ensure the respirator 34 and the pulse oximeter 32 are connected to the same patient 36 and/or that the respirator 34 and pulse oximeter 32 are both properly attached to the patient 36 and functioning. Accordingly, the respirator 34 may be configured to apply small perturbations to the amount of oxygen 35 delivered to the patient 36 over time. Such perturbations should be small enough so as not to interfere with the treatment, yet large enough so that the perturbations are detectable in the oxygen saturation 37 calculated by the pulse oximeter 32 or by any other measurement or calculation made by the device or a connected device. Upon comparing the two, a clinician or control system, such as a control system of the monitoring device and/or therapeutic device, can conclude that the respirator 34 and the pulse oximeter 32 are indeed connected to the same patient 36, and the patient 36 is receiving the designated therapy. On the other hand, if the perturbations in oxygen levels applied by the respirator 34 are not detectable in the measurements of oxygen saturation 37 acquired by the pulse oximeter 32, a clinician or control system may conclude that either the respirator and/or the pulse oximeter 32 are not connected to the same patient or that one of them is not affixed securely to the patient 36 or is not functioning properly.

FIG. 2B illustrates another system in accordance with exemplary embodiments of the present technique. System 50 depicts a diffusion pump 54 and an electrocardiogram (EKG) monitor 52 connected to the patient 56. In this example, the diffusion pump 54 may apply a dose of a medication 55 to the patient intravenously to treat a cardiovascular condition the patient 56 may have. Such a treatment 55 may include a liquefied mixture of substances deliverable to the blood stream of the patient 56. Accordingly, the EKG monitor 52 connected to the patient 56 may be adapted to monitor parameters associated and that are correlated to the cardiovascular activity 57 of the patient 56. Further, measurements obtained by the EKG monitor 52 should indicate the efficacy of the treatment 55 provided to the patient 36. In this example, the system 50 is adapted to perturb the amount of treatment intravenously delivered by the diffusion pump 54 to the patient 36. Correspondingly, the EKG monitor 52 of system 50 may be used for monitoring modulations in cardiovascular activity that are due to the perturbation of the treatment 55 applied to the patient 56. Again, any perturbations in the treatment should be minute enough so as to not adversely affect the quality of the treatment administered to the patient 36, yet substantial enough to be noticeable by the EKG monitor 52. As explained previously, the cardiac activity 57 measured by the EKG monitor 52 may allow the clinician or the control system to make an adjustment to the activity of the diffusion pump 54. Likewise, absence of an indication of perturbations of the treatment 55 in the measured cardiac activity 57 may cause the clinician to check the function and placement of the diffusion pump 54 and/or the EKG monitor 52.

FIG. 2C illustrates another exemplary system 70 in accordance with embodiments of the present technique. The system 70 shows an insulin pump 74, and blood sugar monitor 72 connected to the patient 76. In such a system, insulin 75 may be delivered to the patient 36 via the insulin pump 74 intravenously. Correspondingly, blood sugar levels 77 of the patient 76 may be monitored by the blood sugar monitor 72. Perturbations in the amount of insulin 75 delivered to the patient 76 may be applied as part of a feedback mechanism configured to indicate whether the insulin pump 74 is functional and appropriately attached to the patient 76. Thus, perturbations applied to levels of insulin 75 are expected to be observed by the blood sugar monitor 72, if indeed the blood sugar monitor and the insulin pump 74 are connected to the same patient and are properly functioning. As explained previously, the blood sugar levels 77 measured by the blood sugar monitor 72 may allow the clinician or the system to make an adjustment 79 to the activity of the insulin pump 54. Likewise, absence of an indication of perturbations of the treatment 75 in the measured blood sugar levels 77 may cause the clinician to check the function and placement of the insulin pump 74 and/or the insulin monitor 72.

The systems 30, 50, and 70 described above may also be configured to provide a clinician feedback on how well a specific treatment may be at improving a clinical condition of the patient. Thus, the feedback supplied by the systems 30, 50, and 70 may help the clinician better determine if a present treatment is sufficient or if alternate treatments should be pursued in treating the patient. For example, using system 30, a clinician may want to increase the amount of oxygen 35 delivered to the patient 36 via respirator 34 due to low levels of $SpO_2$ 37, as would be indicated by the pulse oximeter 32. Thus, exemplary systems 30, 50 and 70 and/or others employing the above technique may provide a diagnostic tool for the clinician in evaluating the efficacy of the treatment provided to the patient 36.

Figure 3A:
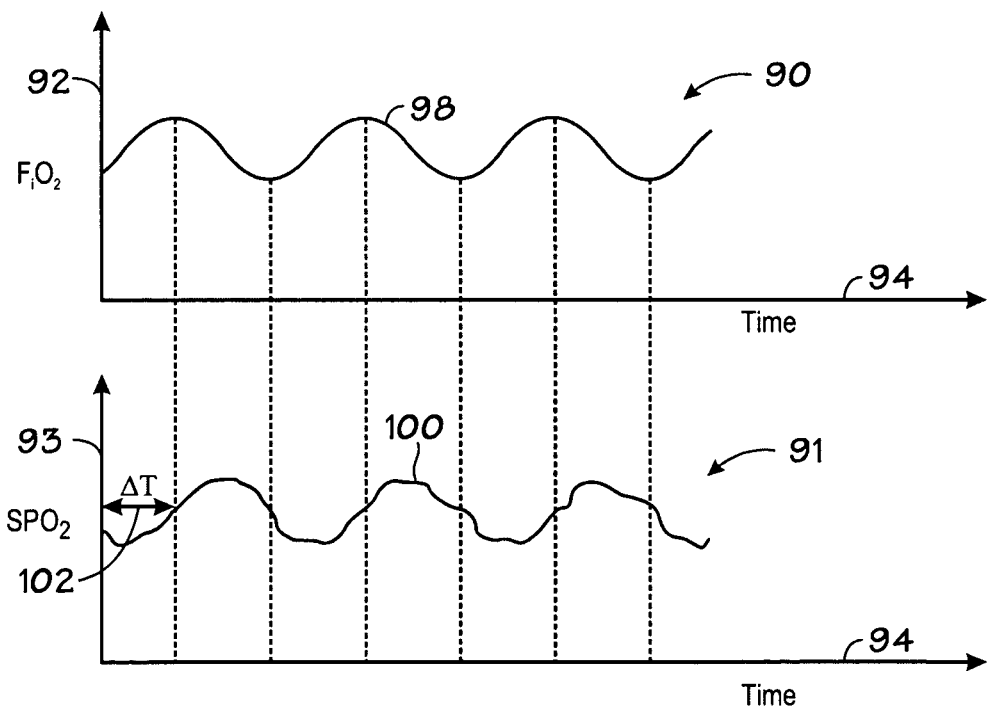
FIG. 3A is a graphical representation in accordance with an exemplary embodiment of the present technique.
Figure 3B:
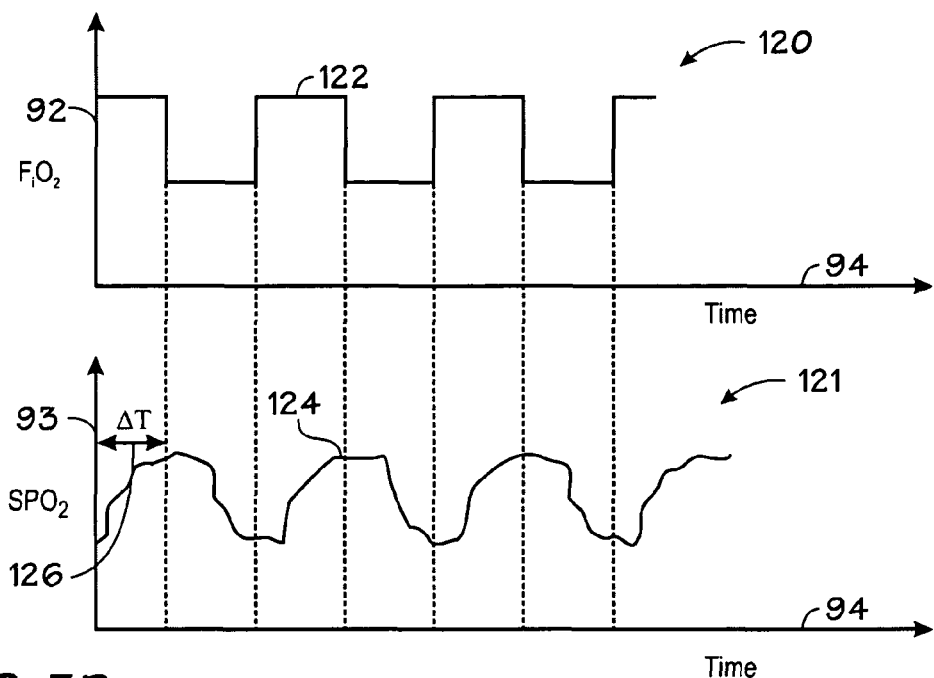
FIG. 3B is a graphical representation in accordance with an exemplary embodiment of the present technique.
Figure 3C:
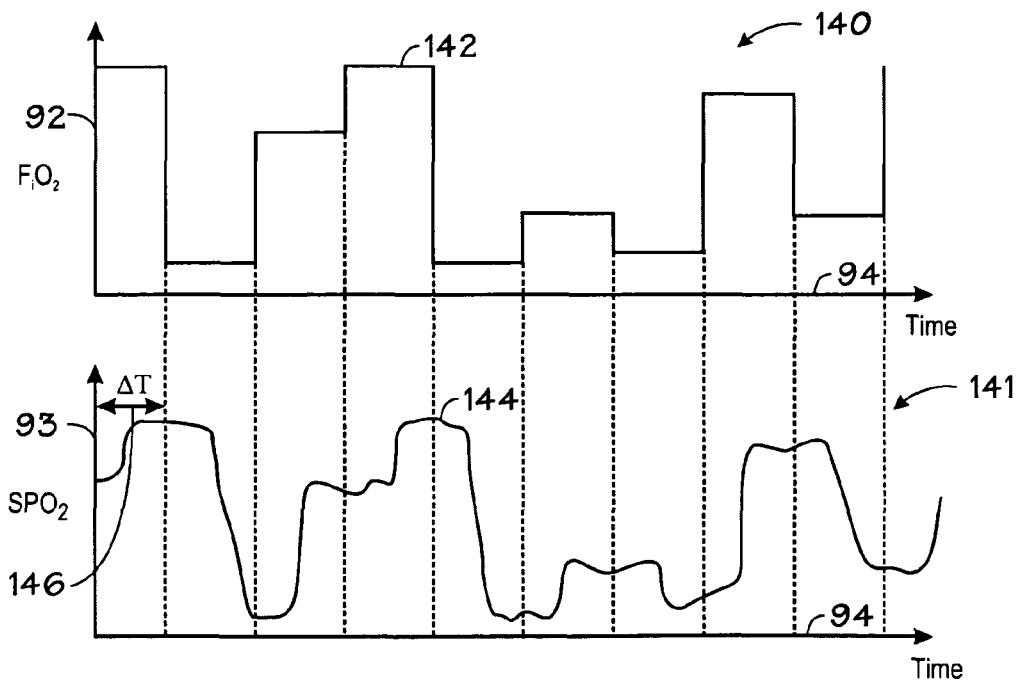
FIG. 3C is a graphical representation in accordance with an exemplary embodiment of the present technique.

FIGS. 3A-3C depict graphical representations in accordance with exemplary embodiments of the present technique. These figures illustrate graphs of exemplary perturbations applied to a specific treatment, and corresponding modulations in a physiological parameter caused by the perturbations over time. Specifically, the graphical representations of FIGS. 3A-3C depict applied perturbations in treatments utilizing a respirator delivering oxygen to a patient, as depicted in FIG. 2A. Accordingly, correlated changes in oxygen saturation levels (SpO2) are depicted as well, showing the effects of the small perturbations in the treatment. It should be appreciated that the technique depicted in the FIGS. 3A-3C is not limited to respirators and pulse oximeters, and could be applied to other treatments having corresponding monitored physiological parameters, as described herein. Among other treatments administered to patients these may include insulin, cardioactive drugs, vasoactive drugs, anesthetic drugs, heating (such as with a heating pad or warming blanket), and/or antipyretic drugs. Physiological parameters associated with such treatments may include blood sugar levels, heart rate, cardiac output, blood pressure, blood perfusion, blood flow, depth of anesthesia, brain activity (such as via an electroencephalograph (EEG)), and/or temperature.

Turning to FIG. 3A, a graphical representation 90 depicts a sinusoidal wave 98, representing periodic perturbations in the fraction inspired oxygen ($FiO_2$) which is the ratio of oxygen to air, delivered to a patient, such as via a respirator. The graph 90 includes a vertical axis 92 denoting $FiO_2$ levels or dose, and a horizontal axis 94 denoting time. Accordingly, the curve 98 is a plot of $FiO_2$ levels administered to a patient over time. Periodic perturbations in graph 90 are manifested in the different $FiO_2$ levels between crest and troughs of the sinusoidal wave 98. It should be appreciated, that these differences are comparatively small to the oxygen level administered to the patient at any point in time. Graph 91 illustrates corresponding modulations in oxygen saturation caused by the perturbations depicted by the curve 98. Accordingly, the graph 91 includes a vertical axis 93, denoting $SpO_2$ levels, and the time axis 94. Curve 100 denotes a corresponding modulated sinusoidal curve indicating levels of oxygen saturation at any moment of time in accordance with the curve 98. As indicated by the curves 98 and 100, a periodic perturbation in the amount of oxygen delivered to the patient corresponds to a periodic modulation in the levels of $SpO_2$. Further, curve 100 is distinguished from curve 98 because of its time shift 102 relative to curve 98. The time shift 102 appearing in the $SpO_2$ level measured by the pulse oximeter is a result of a naturally occurring physiological lag. For example, for a patient breathing oxygen, this lag comprises several breaths to exchange the gas in the lungs, and an additionally circulatory delay for the oxygenated blood to travel from the lungs to the SpO2 sensor site.

FIG. 3B is another exemplary graphical representation of perturbations applied to $FiO_2$ levels and with respective changes in the patient measured as oxygen saturation levels. Accordingly, graph 120 includes curve 122 denoting small periodic changes in $FiO_2$ levels that fluctuate between two constant amounts. Accordingly, the curve 122 comprises a square wave depicting $FiO_2$ levels administered over time to a patient. Graph 121 depicts changes observed in oxygen saturation levels in view of the fluctuating oxygen treatment and in view of the physiological lag described above. As shown by curve 124, changes in the oxygen saturation levels are distinguished from the square wave 122 in that the ramp-up and ramp-down intervals are more gradual. This graded characteristic of curve 124 over time delay 126 is, again, caused by a natural occurring physiological time lag that exists in measuring effects of certain treatments.

FIG. 3C is another exemplary graphical representation of perturbations applied to $FiO_2$ levels and respective changes reflected in oxygen saturation levels. Graph 140 is similar to graph 120 (FIG. 3B) in that it shows periodic perturbations in applied $FiO_2$ levels, however, FIG. 3C depicts that the fluctuations occur between three different $FiO_2$ dosage levels, i.e., three different steps. The perturbations to oxygen levels are shown by curve 142. Thus, perturbations applied by curve 142 are more aperiodic as opposed to the perturbations given by curves 98 and 100. Applying perturbations aperiodically may be advantageous in distinguishing between effects of naturally occurring periodic physiological processes and these fluctuations attributable to perturbing the treatment. Accordingly, graph 141 illustrates curve 144 denoting $SpO_2$ fluctuations in response to the perturbations depicted in a curve 142, as well in response to patient's natural breathing cycles, as indicated small sinusoidal modulations of the curve 144. As shown, curve 144 traces a distinctive gradient pattern as $SpO_2$ levels continuously fluctuate between maximum and minimum levels.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method comprising:
    administering a treatment non-invasively at a specified level to a patient;
    after administration of the treatment has begun and while continuing to provide some level of treatment, temporarily increasing or decreasing the treatment relative to the specified level and returning to the specified level after the temporary increase or decrease, wherein the temporary increase or decrease in the treatment is initiated independently of a change in a parameter indicative of the underlying physiological state of the patient associated with the treatment;
    non-invasively measuring the parameter associated with the treatment;
    evaluating the measured parameter value to determine whether the temporary increase or decrease in the treatment is correlated with the measured parameter value; and
    providing a notification when the temporary increase or decrease in the treatment is not correlated with the measured parameter value within a predetermined period of time after initiation of the temporary increase or decrease; and
    providing a notification that the treatment is being delivered when the temporary increase or decrease in the treatment is correlated with the measured parameter value.

2. The method, as set forth by claim 1, comprising temporarily increasing or decreasing the treatment periodically over time.

3. The method, as set forth by claim 1, comprising increasing or decreasing the treatment aperiodically over time.

4. The method, as set forth by claim 1, wherein the temporary increase or decrease of the treatment is distinguished from a naturally occurring physiological process.

5. The method, set forth by claim 1, wherein the administered treatment comprises oxygen, airway pressure, insulin, heat, a cardioactive drug, a vasoactive drug, an anesthetic drug, and/or an antipyretic drug.

6. The method, set forth by claim 1, wherein the parameter comprises oxygen saturation, heart rate, blood pressure, blood flow, cardiac output, and/or blood perfusion.

7. The method, set forth by claim 1, wherein evaluating the measured parameter value comprises comparing waveforms correlating with the temporary increase or decrease in the administered treatment with waveforms correlating with changes in the parameter or with another measurement or calculation made by a non-invasive monitoring device.

8. The method, set forth by claim 1, comprising alerting a clinician if the temporary increase or decrease in the treatment is not correlated with the parameter.

9. The method, set forth by claim 1, comprising automatically adjusting the treatment if the temporary increase or decrease in the treatment is not correlated with the parameter.

10. The method, set forth by claim 1, comprising automatically adjusting the treatment if the temporary increase or decrease in the treatment is correlated with the parameter.

11. The method, set forth by claim 1, comprising reverting to a prior or predetermined treatment level if the temporary increase or decrease in the treatment is not correlated with the parameter.

12. The method, set forth by claim 1, wherein the notification comprises a message on a display.

13. The method, set forth by claim 1, wherein the notification comprises an audible alarm.

* * * * *